(12) United States Patent
Goldenberg (10) Patent No.: US 7,207,950 B2
(45) Date of Patent: Apr. 24, 2007

(54) ASPIRATION NEEDLE WITH VENTING FEATURE

(76) Inventor: Alec S. Goldenberg, 157 E. 32nd St., Second Floor, New York, NY (US) 10016

( * ) Notice: Subject to any disclaimer, the term of this patent is extended or adjusted under 35 U.S.C. 154(b) by 135 days.

(21) Appl. No.: 11/013,207

(22) Filed: Dec. 14, 2004

(65) Prior Publication Data

US 2006/0089564 A1    Apr. 27, 2006

Related U.S. Application Data

(63) Continuation-in-part of application No. 10/971,302, filed on Oct. 22, 2004.

(51) Int. Cl.
*A61B 10/00* (2006.01)
*A61B 5/00* (2006.01)
*A61M 3/00* (2006.01)

(52) U.S. Cl. ............ 600/562; 600/564; 600/573; 604/45

(58) Field of Classification Search ........ 600/562–567, 600/573; 604/43, 44, 45 X
See application file for complete search history.

(56) References Cited

U.S. PATENT DOCUMENTS 4,808,157 A * 2/1989 Coombs ............... 604/44
5,012,818 A * 5/1991 Joishy ............... 600/567
2002/0087152 A1* 7/2002 Mikus et al. ............ 606/21
2003/0055373 A1* 3/2003 Sramek et al. ........... 604/19

\* cited by examiner

*Primary Examiner*—Max Hindenburg
*Assistant Examiner*—Jonathan Foreman
(74) *Attorney, Agent, or Firm*—Darby & Darby (57) ABSTRACT

An aspirating needle for collecting a specimen including an elongated hollow body that includes a first lumen portion and a second lumen portion. The first lumen portion is open at both ends for placement at a specimen site to collect and permit aspiration of the specimen from the specimen site. The second lumen has first and second vent ports, with the second vent port being formed along the elongated body such that that when the needle is placed at the specimen site, the second vent port is positioned at the specimen site. The first vent port is in fluid communication with atmospheric air when the needle is positioned at the specimen site so as to permit pressure within the specimen site to equilibrate with atmospheric pressure by means of the venting action of the second lumen. In yet another feature, the needle of the present invention includes a handle that permits the appropriate mechanical usage of the needle during a normal operative procedure, with the handle portion of the needle capable of having functionality incorporated therein. The needle can also include a locking mechanism for selectively locking and restricting axial movement of the stylet relative to the first lumen.

26 Claims, 4 Drawing Sheets

ASPIRATION NEEDLE WITH VENTING FEATURE

CROSS-REFERENCE TO RELATED APPLICATION

The present application is a continuation-in-part of U.S. patent application Ser. No. 10/971,302, filed Oct. 22, 2004, which is hereby incorporated by reference in its entirety.

TECHNICAL FIELD

The present invention relates to an instrument, typically known as a needle or cannula that is used to gather a sample from a site using aspiration and more particularly, relates to an aspiration needle for gathering tissue from living persons or animals for pathological study and includes an improved structure for collecting a fluid sample of bone marrow.

BACKGROUND

For various medical reasons, such as diagnostic tests or the like, it is often necessary for a physician to obtain a sample of a specific tissue from a patient Often, a biopsy (sample) is required from a rigid structure, such as a bone or bone marrow. Bone marrow biopsies are typically recovered with significant portions of their internal bony structure intact which allows the pathologist to provide interpretations regarding bone marrow cellularity or possible infiltration with abnormal cells.

A bone marrow sampling procedure usually includes both the collection of a core biopsy using a bone marrow biopsy needle and a fluid sample of bone marrow using an aspiration needle. The two specimens provide complementary information that is relevant for the evaluation of a variety of malignant and nonmalignant hematologic processes. The bone marrow aspiration provides a liquid sample of suspended hematopoietic progenitor cells, stromal cells, and trabecular bone fragments that can be processed for flow cytometric analysis of the bone marrow content, for cytogenetic studies, as well as for the preparation of smears for detailed morphologic evaluation of the progenitor cell morphology. The core biopsy provides accurate information regarding the status of the supporting bone, the cellularity of the bone marrow sample, and the identification of extrinsic cells as seen when the bone marrow is infiltrated with lymphoma or carcinoma.

The process of obtaining both the core biopsy and aspiration sample can produce significant pain for the patient. Specimen capturing needles, including those of the present applicant that are set forth in issued and pending applications, have been designed in an attempt to limit the manipulation of the bone marrow biopsy needle, to increase the recovery of more substantial specimens and to decrease patient pain. However, conventional needles have not been specifically designed to minimize the pain associated with the aspiration process.

Aspiration type needles have a relatively simple design. The needle typically has a sharp tip for puncturing the cortical bone and usually a hub and handle to facilitate the operators guiding the tip safely into the appropriate position. A stylet is left in place until the needle has penetrated the cortex, after which it is removed and an aspirating syringe is placed at the hub. The syringe plunger is rapidly withdrawn to quickly produce a negative pressure which is transmitted through the needle into the bone marrow space to dislodge the material and facilitate its collection into the syringe through the needle. The procedure of quickly pulling back on the plunger and producing a negative pressure usually produces significant pain often described as radiating down the leg. Since the advent of specimen capturing needles, the pain has been described by some patients as being worse than the pain associated with the bone marrow biopsy procedure. An aspirate needle that minimizes patient pain would make the bone marrow procedure more tolerable and acceptable. Moreover, an aspirate needle that minimizes pain would be especially advantageous when multiple aspirates are required to recover a sufficient quantity of bone marrow material for processing.

The exact mechanism that results in the pain and its radiation down into the lower extremity is unknown. It is hypothesized that the introduction of a negative pressure into the bone marrow space stimulates a variety of nerve fibers that results in the pain. Alternatively, simple disruption of the trabecular structure may be the source of the pain.

SUMMARY

An aspirating needle for collecting a specimen is provided and includes an elongated hollow body that includes a first lumen portion and a second lumen portion. The first lumen portion is open at both ends for placement at a specimen site to collect and permit aspiration of the specimen from the specimen site. The second lumen has first and second vent ports, with the second vent port being formed along the elongated body such that that when the needle is placed at the specimen site, the second vent port is positioned at the specimen site. The first vent port is in fluid communication with atmospheric air when the needle is positioned at the specimen site so as to permit pressure within the specimen site to equilibrate with atmospheric pressure by means of the venting action of the second lumen.

The aspiration needle of the present invention finds particular utility in an application where tissue is gathered from living persons or animals for pathological study and more specifically, the venting feature of the needle provides an improved structure for collecting a fluid sample of bone marrow.

In yet another feature, the needle of the present invention includes a handle that permits the appropriate mechanical usage of the needle during a normal operative procedure. A stylet sits within the second lumen portions. The needle can include a locking mechanism for selectively locking and restricting axial movement of the stylet relative to the first lumen. This is desirable since during insertion of the needle through tissue to reach the specimen site, it is not desirable for the stylet to move relative to the needle itself since the stylet serves to locate and position the needle at the specimen site. In one embodiment, the locking mechanism includes a first locking feature, such as a projection or channel, formed as part of the stylet and a complementary second locking feature, such as a channel or a projection, formed as part of the elongated body. In other embodiments, the handle portion of the needle has functionality incorporated therein. For example, the handle can include a portion of the vent conduit that is the second lumen, thereby permitting one vent port to be formed in the handle itself. This can make it easier for a filter element to be inserted and removed from this vent port. In addition, the handle can include a reservoir that is in fluid communication with a conduit formed at least in part in the second lumen and in this embodiment, the conduit is for delivery of a material, such as a therapeutic gel, medicine, or glue, from the reservoir to the specimen site. The reservoir can have a vent port to expose it to atmospheric conditions to permit the material to be drawn down the conduit and out of the vent port at the specimen site.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which.

DETAILED DESCRIPTION OF THE PREFERRED EMBODIMENT

Figures 1, 2:
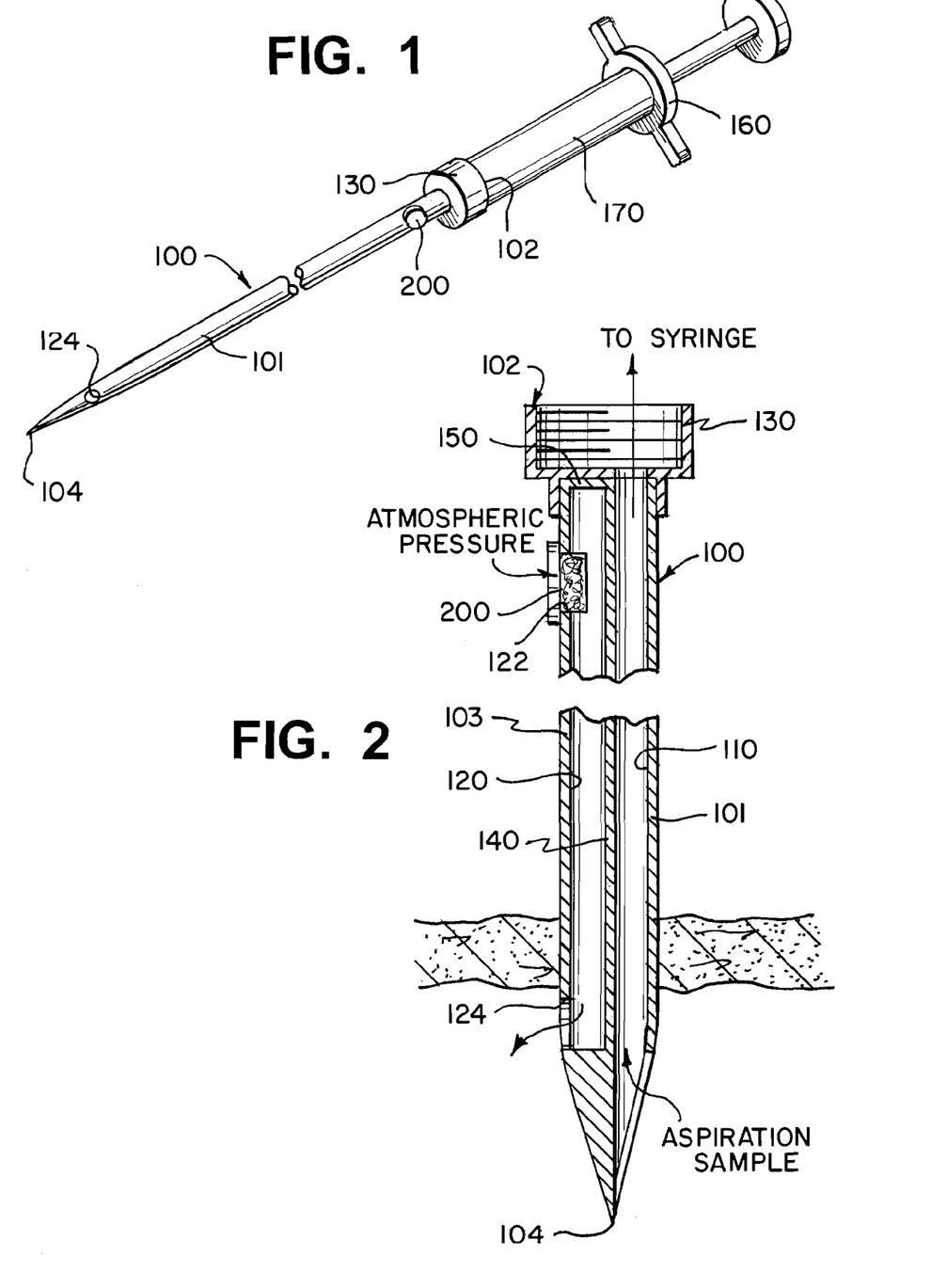
FIG. 1 is a perspective view of an aspiration needle according to a first embodiment for use at a site that is aspirated to collect a sample, such as a fluid sample of bone marrow.
FIG. 2 is a cross-sectional view of the aspiration needle of FIG. 1.

Referring now to FIGS. 1 and 2, an aspiration needle 100 according to one exemplary embodiment is illustrated and is particularly suited for use at a target site, such as one associated with a bone marrow aspiration application. In other words, while the aspiration needle 100 is particularly suited for use in medical applications where aspiration of a local site takes place, it will be understood that the needle 100 is suited for other applications in which equilibration of the aspirated space is desirable. It is contemplated that there are additional non-medical applications for the aspiration needle 100 with one potential application being a manufacturing type application or a laboratory application where equilibration is needed.

The aspiration needle 100 is constructed to overcome the deficiencies associated with conventional bone marrow aspiration needles and more specifically, is constructed to minimize the potential negative pressure that develops during the bone marrow collection and aspiration process. In order to achieve this goal, the needle 100 includes a type of "vent" that modulates the pressure in the bone marrow space as the material is withdrawn.

The needle 100 has a first end 102 that is a proximal end and an opposing second end 104 that is a distal end. The second end 104 (distal end) is the sharp tip end for puncturing the cortical bone during the bone marrow collection procedure. The needle 100 is based on a double lumen design in that the needle 100 includes a first lumen 110 and a second lumen 120 that is proximate the first lumen 110. The first lumen 110 acts as a conduit for material to be withdrawn out of a bone marrow space into a syringe 160, while the second lumen 120 allows the pressures within the bone marrow space to equilibrate with outside pressures. The needle 100 is securely coupled to the syringe 160 using conventional techniques, such as threaded fastening means. The syringe 160 include a collection chamber 170 (barrel chamber) for collecting the sample that is aspirated through the needle 100.

The first end 102 has a feature 130 that permits the needle 100 to be coupled to another component and therefore, can include a flange, cap, coupling member or the like. The first end 102 can serve as or be coupled to a hub and handle to facilitate the operators guiding the second end 104 safely into the appropriate position. The needle 100 shares a number of characteristics that are basic to most needles in that that the needle 100 is defined by an elongated structure (body 101) that is hollow in nature from one end 102 to the other end 104. The needle 100 can have any number of different shapes and for purpose of illustration only, the illustrated needle 100 has a circular cross-section; however, it will be appreciated that the cross-section of the needle 100 can be other shapes, including but not limited to square shaped, rectangular shaped, triangular shaped, etc.

The division of the body 101 of the needle 100 can be accomplished in any number of different ways so long as the body 101 is divided into the first lumen 110 and the second lumen 120. For example, the needle 100 can include a dividing or partitioning wall 140 that is formed within the body 101 and serves to partition at least a length of the interior of the body 101 into the first and second lumens 110, 120. It will be appreciated that the wall 140 does not have to evenly divide the interior of the body 101 such that the first and second lumens 110, 120 occupy the same area but rather the first and second lumens 110, 120 can occupy different amounts of areas. Thus, while FIG. 1 shows the wall 140 generally evenly dividing the interior of the body 101 into the first and second lumens 110, 120, this is merely exemplary and illustrative in nature as opposed to being limiting. For example, the second lumen 120 that is associated with performing a venting operation can occupy less area than the first lumen 110 which serves as the conduit for withdrawing the bone marrow or sample material. Another embodiment is one where the divider 140 is eliminated and a tube, possibly flexible, is provided within the body of the needle 101 with one end of the tube exiting at the lumen 122 and the other exiting or connected to the lumen or vent 124.

The first lumen 110 is thus a generally unobstructed channel that extends from the first end 102 to the second end 104 and therefore, it permits material to be aspirated into the distal second end 104 and withdrawn to the first end 102 in a generally linear manner. Conversely, the second lumen 120 is not constructed to receive material at the bone marrow site (space) but rather, the second lumen 120 is constructed to permit atmospheric air to be delivered to the bone marrow site so as to serve as a vent and allow the pressure within the bone marrow space to equilibrate with outside pressures, e.g., atmospheric pressure.

In the illustrated embodiment, the second lumen 120 has a first open end 122 and an opposing open second end 124, with the first end 122 being proximate or close to the first end 102 of the needle 100 and the second end 124 being proximate or close to the second end 104 of the needle 100. As shown in FIG. 1, the open second end 124 is in the form of a vent port or opening that is formed in a side surface 103 of the body 101 as opposed to being formed directly at the second end 104. The vent port 124 is preferably formed in the side surface 103 either at or close to the second end 104 since the vent port 124 is to be in fluid communication with the bone marrow space when the distal end 104 of the needle 100 is inserted and guided to the bone marrow collection site (space). The open first end 122 is also formed in the side surface 103 either at or close to the first end 102 and is in the form of a vent port or opening that is in fluid communication with atmospheric air (pressure) when the needle 100 is properly used and the distal tip 104 is guided to the bone marrow site (space). Between the vent ports 122, 124, the second lumen 120 is defined by a longitudinal (linear) channel that is formed between an inner surface of the side surface or wall 103 and the partitioning wall 140. In order for the first opening 122 to serve as a vent port, the second lumen 120 is preferably closed at the first end 122 by a structure 150, such as wall that extends across the channel that defines, in part, the second lumen 120. The structure 150 does not extend across or in any way obstruct the first lumen 110 since the first lumen 110 is completely open at both ends to permit collection and withdrawal of the sample from the bone marrow space. The closing structure 150 is thus located proximate to the vent port 122. The distance between the two vent ports 122, 124 is such that when the distal second end 104 is guided and positioned at the bone marrow space, the vent port 122 is located outside or exterior to the patient and in fluid communication with atmospheric air.

Optionally and preferably in a number of applications, the needle 100 includes a filter 200 which is associated with the second lumen 120 to remove any physical or bacterial particles that might be drawn into the space (channel) during the procedure. The filter 200 can be placed in any number of different locations, including within the side wall and along the channel that extends between the first and second vent ports 120 or, as illustrated, the filter 200 can be placed in the first opening 122. By positioning the filter 200 at the first opening (vent port) 122, the filter 200 can easily be accessed and changed, inspected or replaced with a different type of filter 200. The filter 200 can be held within the vent port 122 using conventional techniques, including establishing a frictional fit between the filter 200 and the walls of the vent port 122. The use of an adhesive material or other techniques can equally be used so long as the filter 200 is secured in place and air flowing between the vent ports 122, 124 passes through the filter 200.

While the double lumen type needle of FIG. 1 illustrates one exemplary needle construction, it will be appreciated that the needle 100 can have a number of different constructions and can be manufactured in a number of different ways. For example, the creation of the first and second lumens 110, 120 can result from inserting or forming a divider, such as wall 140, within a single lumen tube (body 101), resulting in the formation of double lumen. The divider is then sealed against the single lumen to maintain a vacuum therein. Alternatively, two single lumen tubes could be coupled together, as by a bonding or welding operation or adhesives, etc., to produce a double lumen tube. In yet another embodiment, a tube with a smaller diameter can be inserted into a tube with a larger diameter thereby producing a double lumen tube. Moreover, the inserted tube might not necessarily have to be made of stainless steel but instead could be constructed of a small diameter plastic tube, while the other tube could be constructed of a stainless steel to provide the stability for cortical puncture.

Figure 3:
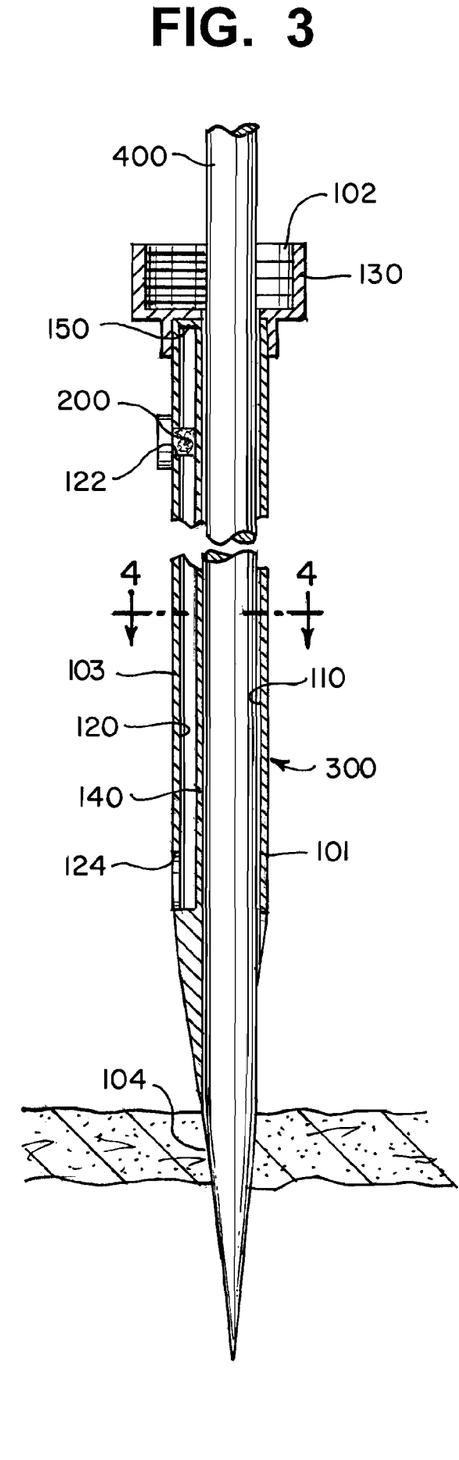
FIG. 3 is a cross-sectional view of an aspiration needle according to a second embodiment.
Figure 4:
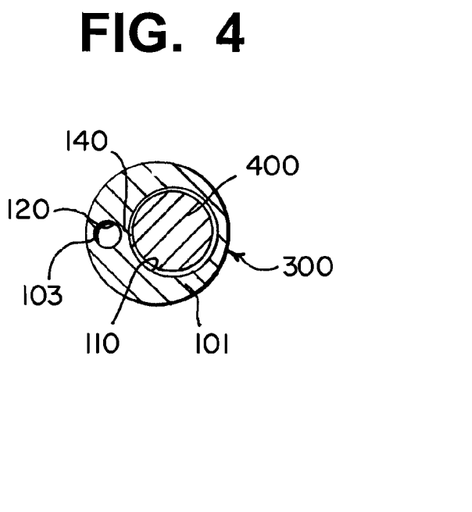
FIG. 4 is a cross-sectional view taken along the line 4—4 of FIG. 3.

FIGS. 3–4 illustrate a needle 300 being used in combination with a stylet 400. The needle 300 is very similar to the needle 100 and therefore, like elements are numbered alike.

In this embodiment, the relative areas of the first and second lumens 110, 120 are shown and more particularly, the first lumen 110 occupies significantly more cross-sectional area than the second lumen 120 since the first lumen 110 receives and permits aspiration of the sample to the collection chamber 170 (FIG. 1); while the second lumen 120 performs a venting action and only needs to permit air to pass therealong. The cross-sectional area of the second lumen 120 should be such that it does not produce a resistance to airflow and permits the desired venting action.

It will be appreciated that the ratio of the cross-sectional areas between the first and second lumens 110, 120 is variable depending upon the particular given application; however, the dimensions of the second lumen 120 is such that it does not produce a resistance to airflow but instead vents the air. For example, the cross-sectional area of the second lumen 120 compared to the entire cross-sectional area of the needle 100 can be on the order of between about 1% to about 40% in one embodiment, between 10%–30% in another embodiment; and 15%–25% in another embodiment. However, these values are merely exemplary in nature and are not limiting of the present scope of the present invention in any manner.

The stylet 400 as you know is placed within the needle 300 and has a tip to it which allows the needle 300 to puncture the cortex. The stylet 400 is removed once the needle 300 has penetrated the cortex opening up the first lumen 110 for the aspiration procedure. In this needle design, the stylet 400 will initially sit within the first lumen 110 that carries the material from the bone marrow to the syringe and not in the venting lumen (second lumen 120).

Figures 5, 6, 7:
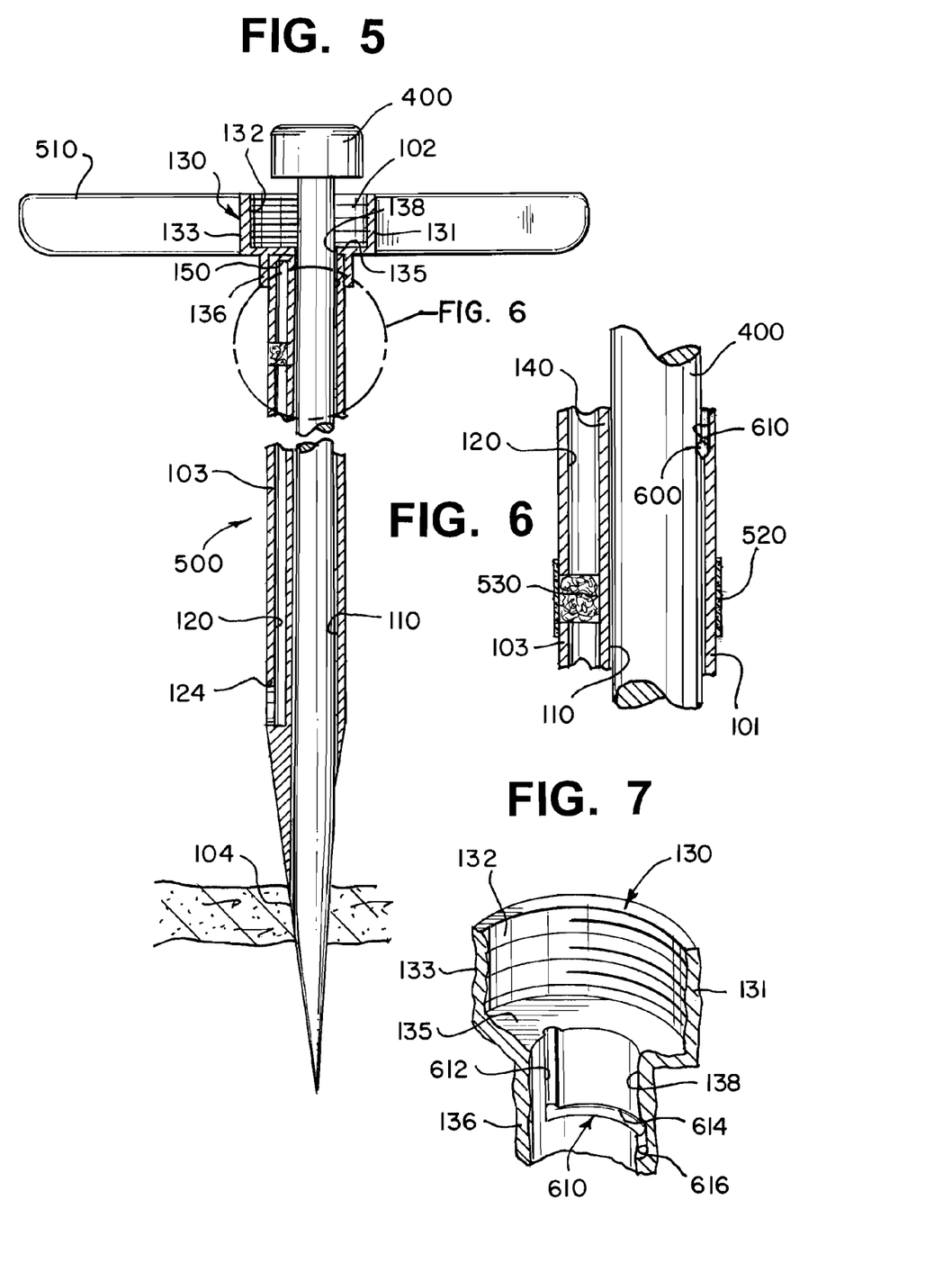
FIG. 5 is a cross-section view of an aspiration needle according to a second embodiment.
FIG. 6 is a perspective view, in partial cross-section, of a stylet within the aspiration needle of FIG. 5 illustrating a locking feature thereof.
FIG. 7 is a perspective view, in partial cross-section, of a top portion of the needle illustrating the stylet locking feature.

Now referring to FIGS. 5–7 in which an aspiration needle 500 is illustrated. Needle 500 is similar to needle 100 and therefore, like elements are numbered alike in FIGS. 5–7. The needle 500 therefore preferably has a double lumen design and is defined by the first lumen 110 and the second lumen 120 proximate (e.g., adjacent) the first lumen 110. The first lumen 110 acts as a conduit for material to be withdrawn out of a bone marrow space into the collection member 160 (FIG. 1), which can be a syringe or the like, while the second lumen 120 allows the pressures within the bone marrow space to equilibrate with outside pressures. The needle 500 includes at the first end 102 a fastening means 130 that permit the needle 500 to be securely yet releasably attached to the collection member 160.

For example and as illustrated, the fastening means 130 is in the form of a wall structure 131 that is dimensioned and shaped so as to receive at least a portion of the collection member 160 between the wall structure 131. In other words, the fastening means 130 is preferably a female feature that receives the collection member 160 which is in the form of a male feature. In the illustrated embodiment, the wall structure 131 has an annular shape and includes an inner wall surface 132 and an outer wall surface 133. The diameter of the wall structure 131 can be greater than the diameter of the elongated needle portion (lumens 110, 120) that lies and therefore, a floor or landing 135 can be formed at the bottom of the fastening means 130. The inner surface 132 preferably includes some fastening feature that mates with a complementary fastening feature formed as part of a connector portion of the collection member 160 such that when the two fastening features mate together, the collection member 160 securely attaches to the needle 500. In the illustrated embodiment, the inner surface 132 includes a series of threads that permit the collection member 160 to threadingly mate with the wall structure 131. To release the collection member 160, it is merely twisted in an opposite direction so as to unthread the two from one another.

The fastening means 130 can be an integral part of the needle 500 or it can be a separate part that is securely fitted to the upper end of the two lumens 110, 120. In other words, the fastening means 130 can include a connector portion 136 (e.g., a boss structure or the like) that can be frictionally fitted around the outer periphery of the upper end of the needle 500. The floor 135 acts as a stop and limits the degree of travel of the needle 500 within the inside of the connector portion 136. The floor 135 includes a central opening 138 that receives the stylet 400.

The needle 500 includes a handle 510 that permits and allows the appropriate mechanical usage of the needle 500. During the normal use of the needle 500, the physician or operator has to apply a sufficient force against the needle 400 to drive the needle through tissue and the like in order to locate and place the needle tip 104 at the operative site, e.g., a bone marrow site. More particularly, the stylet 400 is introduced into the first lumen 110 through the opening 138 of the fastening means 130 and is advanced therein until it extends beyond the second end 104. As mentioned above, the stylet 400 is used to initially place and locate the needle 400 at the operative site. A significant amount of force is therefore required to direct the needle through tissue and therefore, the handle 510 provides a spot where the operator can hold and apply force against the needle body.

The handle 510 can be located at any number of different locations along the body of the needle 500. For example, the handle 510 can be integrally formed along the length of the lumens 110, 120 or, as illustrated, the handle 510 can be integrally formed as part of the fastening means 130. The handle 510 likewise can have any number of different shapes and can have an annular shape where it extends around the complete periphery of the needle body or it can be in the form of one or more fingers or tabs that extend outwardly from the needle body (e.g., from lumens 110, 120 or fastening means 130). In FIG. 5, the handle 510 is in the form of a pair of opposing fingers or tabs that are curved or rounded at a distal end to permit the operator to place either two fingers against the two handle tabs or place fingers of two hands against the two handle tabs.

The needle 500 also incorporates a stylet locking feature that functions to selectively lock the stylet 400 in place relative to the body of the needle 500. More specifically, the stylet locking feature is defined by a first stylet guide/lock feature 600 that is associated with the stylet 400 and a complementary second stylet guide/lock feature 610 that is associated with the body 101 of the needle 500. The first feature 600, in the illustrated embodiment, is a nub or projection that protrudes outward from the outer surface of the stylet 400 and the second feature 610 is a contoured channel formed in either the inner surface 132 of the fastening means 130 or the inner surface of the elongated body of the needle 500 (as shown in FIGS. 5–7). For example, FIG. 7 shows the channel 610 formed below the floor 135 and along the inner surface of the first lumen 110.

The illustrated channel 610 is defined by a number of segments, such as a receiving channel segment 612, a transverse channel segment 614, and a lock segment 616, with the transverse channel segment 614 being formed between ends of the channel segments 612, 616. In fact, an entrance to the receiving channel segment 612 is formed in the floor 135 and is a vertical channel that extends to a point where the transverse channel segment 614 is formed. The transverse channel segment 614 is thus a horizontal channel that is formed perpendicular to the vertical channel segment 612. The lock segment 616 is another vertical channel segment that is formed at the opposite end of the transverse channel segment 614 and is therefore, perpendicular thereto.

The stylet 400 interacts and locks with the needle 500 in the following manner. First, the first feature 600 (nub/projection) is aligned with the first channel segment 612 and is received therein. The stylet 400 is then advanced in the first lumen 110 which causes the nub 600 to ride down the vertical channel 612 and when it reaches the bottom or end of the vertical channel 612, the stylet 400 is rotated so as to cause the nub 600 to travel the length of the transverse channel 614 toward the lock channel segment 616. Once the nub 600 reaches the end of the transverse channel 614 it is axially aligned with the lock channel segment 616. To lock the stylet 400 in the axial distance relative to the needle 500, the stylet is further axially advanced within the first lumen 110, thereby causing the nub 600 to advance within the lock channel segment 616 until it reaches an end thereof. When the nub 600 is disposed at the bottom of the vertical lock channel segment 616, the stylet 400 can not be further axially advanced within the first lumen 110. In this locked position, the needle 500 and stylet 400 are ready to be inserted and advanced through the tissue until the stylet 400 and the tip 104 are disposed at the operative site (e.g., bone marrow site).

It will be appreciated that the lengths of the channel segments 612 and 616 define the length of travel of the stylet 400 within the needle 500 and therefore, these lengths are selected such that when the nub 600 travels into and is locked in the lock channel segment 616, the stylet 400 can no longer extend further axially within the first lumen 110. In other words, the stylet 400 can not be further advanced within the first lumen 110 and thus, when the nub 600 is locked in the lock channel segment 616, the stylet 400 is at its most distal point (i.e., its distal tip is at a maximum distance beyond the distal end 104 of the needle). To release the stylet 400, the process is simply reverse in that the stylet 400 is pulled up causing nub 600 to travel up to the transverse channel 614, the stylet 400 is then rotated till the nub 600 is aligned with the vertical channel 612 and then the stylet 400 is lifted up (nub 600 travels in vertical channel 612) till the nub 600 clears the floor 135.

It will also be understood that the first and second features 600, 610 can be reversed in that the first feature 600 can be channel formed in the outer surface of the stylet 400 and the second feature can be a nub or projection formed on the inner surface 132 of the fastening means 130 or on the inner surface of the needle 500 (e.g., first lumen 110). The two features 600, 610 complement each other in the same manner as those described above in that the stylet 400 is simply rotated and axially moved within the first lumen 110.

In yet another feature, needle 500 includes a different type of filter medium compared to filter 200 shown in FIG. 2. More specifically, the needle 500 includes a filter band 520 that is an elastic band like member that can be stretched and then fitted securely around the outer surface of the needle 500. After the band 520 is stretched to permit it to be fitted around the circumference of the needle 500, the band 520 is released and the elastic properties thereof cause the band 520 to constrict and is held against the outer surface of the needle 500. The band 520 interacts with a filter element 530 so as to locate and position the filter element 530 over or within the first vent port 122 such that air flowing into the first vent port 122 flows through the filter element 530. For example and according to one embodiment, the filter element 530 is separate from the band 520 and is at least partially inserted into the first vent port 122. The band 520 is then placed and fitted around the periphery of the needle 400 such that the band 520 at least partially covers the filter element 530. This results in the filter element 530 being fixed within the first vent port 122. Alternatively, the S filter element 530 can actually be incorporated directly into the structure of the band 520 itself. In other words, a portion or length of the band 520 comprises the filter element 530. In this embodiment, the band 520 is fitted around the periphery of the needle 500 so as to position and locate the filter element 530 over and/or at least partially within the first vent port 122.

Figure 8:
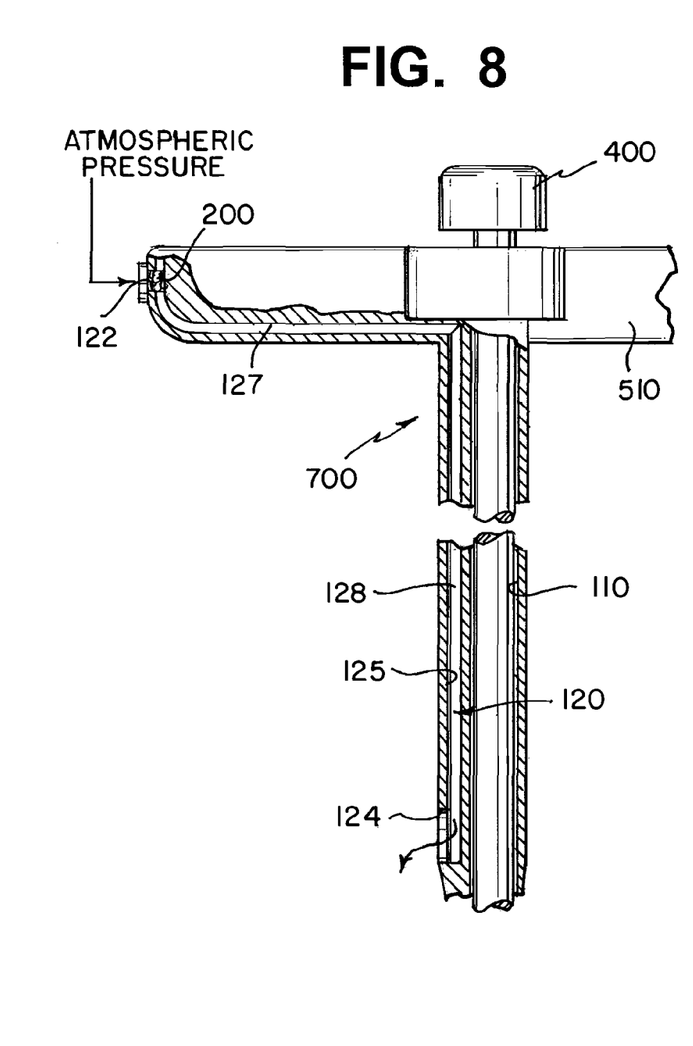
FIG. 8 is a perspective view, in partial cross-section, of an aspiration needle according to a third embodiment.

Now referring to FIG. 8, an aspiration needle 700 according to a third embodiment is illustrated. Once again, the needle 700 is similar to both needles 100 and 500 and therefore, like elements are numbered alike. In this embodiment, the needle 700 includes handle 510; however, the handle 510 is configured such that it is in fluid communication with the second lumen 120 and more particularly, at least a portion of the vent channel that extends between the two vent ports 122, 124 is formed in the handle 510 itself. More specifically, the second lumen 120 includes a vent channel 125 that extends between the first vent port 122, which in this case is formed in the handle 510 and the second vent port 124 which is formed in the side wall of the needle 700.

The illustrated vent channel 125 is defined by two sections, namely a first channel segment 127 which is formed substantially within the handle 510 and comprises a transverse channel and a second channel segment 128 which is formed along the length of the needle 700 and thus, represents a vertical channel. The first and second channel segments 127, 128 intersect one another at preferably a right angle.

One reason for extending the vent channel 125 into the handle 510, as shown in FIG. 8, is that is permits the filter element 200 to be more easily inserted into the first vent port 122 since the handle 510 can have a larger surface areas than the side of the needle 700 and thus, it is more easy to form the first vent port 122 in the handle 510 as opposed to the side wall of the needle as shown in FIG. 2. In other words, when the vent port 122 is formed in the handle 510, it can be much larger and therefore, it can receive a larger filter element 200. In this manner, it is less likely that the filter element 200 has to be tailored to fit within a small opening as could be the case when the vent port 122 is formed in the side of the needle 700. As shown in FIGS. 1 and 8, the filter element 200 can be in the form of a plug which is inserted into the vent port 122 and includes a plug body that holds a filter material such that air passes through the filter material to enter into the vent channel 125.

In the illustrated embodiment, the first vent port 122 and thus the filter element 200 are shown in the peripheral (circumferential) side edge of the handle 510; however, this is merely one location with a number of other locations on the handle 510 being equally suitable. For example, the first vent port 122 can be formed on a topside or an underside of the handle 510. Once again, the function of the vent channel 125 is to deliver air/expose the operative site with atmospheric pressure.

Figure 9:
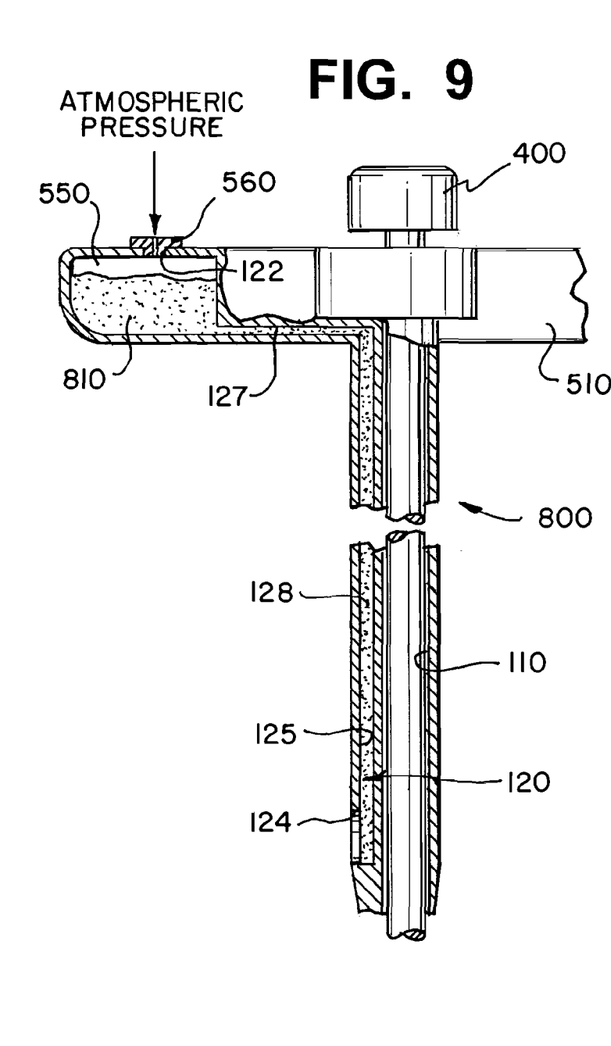
FIG. 9 is a perspective view, in partial cross-section, of an aspiration needle according to a fourth embodiment.

Now referring to FIG. 9 in which a needle 800 according to another embodiment of the present invention is illustrated. In this embodiment and similar to the embodiment illustrated in FIG. 8, the handle 510 has functionality incorporated or formed therein. More precisely, the handle 510 include the first channel segment 127 which is formed substantially within the handle 510 and the second channel segment 128 which is formed along the length of the needle 800 and intersects the first channel segment 127 at a right angle. Instead of having simply a filter element in communication with the first channel segment 127 in the handle 510, the needle 800 is configured to use a vented aspirating needle system for the application of therapeutic gels, glues, and medications (material 810). It is sometimes difficult to inject material directly into a tissue since the tissue and the tissue fluid volume is often limited by tissue or organ compartments or capsules. Therefore to place a certain volume of material into a nonvascular tissue it may be appropriate to aspirate or remove a certain volume and to replace that volume with the appropriate medication or material. The vented aspiration needle could be used to facilitate the installation of materials into tissues with fixed tissue and fluid volumes. In other words, the aspirating lumen (second lumen 120) could be used as a conduit to remove a certain volume of fluid or tissue and the venting lumen (second lumen 120) could provide a conduit for replacing the volume not with air but with another fluid or gel in a coordinated fashion.

In the illustrated embodiment, the handle 510 include a reservoir 550 formed therein and in fluid communication with the first channel segment 127 so as to permit the flow of material within the reservoir 550 from the reservoir 550 into the first channel segment 127 and then ultimately into the second channel segment 128 to the port 124 which is an exit port for the material. The handle 512 preferably includes port 122 which is an opening that directly leads to the reservoir 550 to permit filling of the reservoir 550 of the material. The port 122 is plugged with a removable cap 560. In order to permit flow of the material in the channel 125, the cap 560 preferably is a vented cap (and can contain a filter element) so as to expose the reservoir 550 with atmospheric pressure to permit and facilitate the flow of material through channel 125 and out of the port 124. Thus, when the needle 800 is placed with its tip 104 at the operative site and exposed to the internal pressure at the operative site, the pressure differential causes the material to flow through the channel 125 towards the vent port 124 where it exits into the operative site.

It will be appreciated that the locking mechanism of the present invention can be different than the ones disclosed herein so long as it functions in the same manner and achieves the same results. More particularly, the locking mechanism has a locked position in which the stylet is locked in place relative to the needle and is locked such that the stylet can not be further axially advanced in the first lumen portion. When the stylet is in the locked position, a prescribed length thereof extends beyond the needle and is accessible for locating the needle tip at the specimen site. The locking of the stylet must be constructed such that it can withstand the forces generated against the stylet as the stylet encounters and pierces tissue, etc. Once the stylet is at the specimen site, it is then required for the stylet to be easily unlocked and removed from the needle. The locking mechanism should therefore be simple yet effective. Other types of locking mechanisms beyond the illustrated ones can be used in the practice of the present invention so long as the locking mechanisms serve to lock and prevent axial movement of the stylet within the first lumen portion. It is also desirable, as shown in the illustrated embodiments, that the locking mechanism restricts free rotation of the stylet within and relative to the first lumen portion so as to prevent unduly rotation of the stylet as it is advanced to the specimen site.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. An aspirating needle for collecting a specimen comprising:
   an elongated hollow body that includes a first lumen portion and a second lumen portion, the first lumen portion being open at both ends for placement at a specimen site to collect and permit aspiration of the specimen from the specimen site, the second lumen having first and second vent ports, with the second vent port being formed along the elongated body such that that when the needle is placed at the specimen site, the second vent port is positioned at the specimen site, the first vent port being in fluid communication with atmospheric air when the needle is positioned at the specimen site so as to permit pressure within the specimen site to equilibrate with atmospheric pressure by means of the venting action of the second lumen;
   a handle that is part of the elongated body to permit a force to be applied to the needle for directing the needle to the specimen site;
   an elongated stylet for insertion into the first lumen;
   a locking mechanism for selectively locking and restricting axial movement of the stylet relative to the first lumen; and
   a filter disposed within the second lumen to remove particles drawn into the second lumen during an aspiration procedure.

2. The aspirating needle of claim 1, wherein the first and second vent ports are formed in a side wall of the needle body.

3. The aspirating needle of claim 1, wherein the first and second lumens are disposed adjacent one another and extend longitudinally side-by-side for at least a substantial length of the needle.

4. The aspirating needle of claim 1, wherein the body includes a partitioning structure that extends longitudinally therein and divides an interior of the body into the first and second lumens.

5. The aspirating needle of claim 1, wherein the needle includes a sharp distal end with the first lumen being open at the distal end to receive and permit the stylet to exit through the opening and extend beyond the distal end of the needle.

6. The aspirating needle of claim 1, wherein the locking mechanism includes a first locking feature formed as part of the stylet and a complementary second locking feature formed as part of the elongated body.

7. The aspirating needle of claim 6, wherein the first locking feature comprises a projection formed on an outer surface of the stylet and the second locking feature comprises a channel formed in an inner surface of the elongated body, the channel receiving the projection and being constructed to restrict axial movement of the stylet in the first lumen when the stylet is placed in a locked position in the channel.

8. The aspirating needle of claim 7, wherein the locking channel is formed along the inner surface of the first lumen and includes a first segment that receives the projection, a traverse segment having a first end in communication with one end of the first segment and a locking segment formed at and in communication with an opposite second end of the transverse segment, wherein the projection is disposed in the locking channel when the stylet is in the locked position.

9. The aspirating needle of claim 8, wherein the first segment and the locking segment are parallel to one another and are formed at a right angle to the transverse segment.

10. An aspirating needle for collecting a specimen comprising:
    an elongated hollow body that includes a first lumen portion and a second lumen portion, the first lumen portion being open at both ends for placement at a specimen site to collect and permit aspiration of the specimen from the specimen site, the second lumen having a vent conduit including a distal vent port formed along the elongated body such that that when the needle is placed at the specimen site, the distal vent port is positioned at the specimen site;
    a handle that is coupled to the elongated body to permit a force to be applied to the needle for directing the needle to the specimen site;
    an elongated stylet for insertion into the first lumen;
    wherein the conduit also includes a proximal vent port in fluid communication with atmospheric air when the needle is positioned at the specimen site so as to permit pressure within the specimen site to equilibrate with atmospheric pressure by means of the venting action of the conduit and at least a portion of the vent conduit, including the proximal vent port, is formed in the handle; and
    a filter disposed within the proximal vent port to remove any physical or bacterial material that is drawn into the second lumen during an aspiration procedure.

11. The aspirating needle of claim 10, wherein the portion of the second lumen formed in the handle comprises a transverse channel segment that is in fluid communication with a vertical channel segment formed in the second lumen and terminating at the distal vent port, the transverse and vertical channel segments defining the vent conduit.

12. The aspirating needle of claim 11, wherein the transverse channel segment and the vertical channel segment are formed at a right angle relative to one another.

13. The aspirating needle of claim 12, wherein the first lumen and the vertical channel segment of the second lumen are disposed adjacent one another and extend longitudinally side-by-side for at least a substantial length of the needle.

14. The aspirating needle of claim 10, further including:
    a locking mechanism for selectively locking and restricting axial movement of the stylet in the first lumen.

15. The aspirating needle of claim 14, wherein the locking mechanism includes a first locking feature formed as part of the stylet and a complementary second rocking feature formed as part of the elongated body.

16. The aspirating needle of claim 15, wherein the first locking feature comprises a projection formed on an outer surface of the stylet and the second locking feature comprises a channel formed in an inner surface of the elongated body, the channel receiving the projection and being formed to restrict axial movement of the stylet in the first lumen when the stylet is placed in a locked position in the channel.

17. The aspirating needle of claim 16, wherein the locking channel is formed along the inner surface of the first lumen and includes a first segment that receives the projection, a traverse segment having a first end in communication with one end of the first segment and a locking segment formed at and in communication with an opposite second end of the transverse segment, wherein the projection is disposed in the locking segment when the stylet is in the locked position.

18. An aspirating needle for collecting a specimen comprising:
  an elongated hollow body that includes a first lumen portion and a second lumen portion, the first lumen portion being open at both ends for placement at a specimen site to collect and permit aspiration of the specimen from the specimen site, the second lumen having a conduit formed therein that terminates at a distal port formed along the elongated body such that when the needle is placed at the specimen site, the distal port is positioned at the specimen site;
  a handle that is coupled to the elongated body to permit a force to be applied to the needle for directing the needle to the specimen site;
  an elongated stylet for insertion into the first lumen;
  wherein at least a portion of the conduit is formed in the handle and the handle includes a reservoir that is in fluid communication with the conduit and is constructed to hold a material that is for introduction to the specimen site by traveling within the conduit and being discharged through the distal port; and
  a filter disposed in a plug that is removably disposed within a proximal port that is formed in the handle and forms an entrance into the reservoir, the filter being constructed to remove material that is drawn into the conduit during an aspiration procedure.

19. The aspirating needle of claim 18, wherein the material is selected from the group consisting of a therapeutic gel, a glue, and one or more medications.

20. The aspirating needle of claim 18, wherein the portion of the conduit formed in the handle comprises a transverse channel that is in fluid communication with a vertical channel formed in the second lumen and terminating at the distal port.

21. The aspirating needle of claim 20, wherein the transverse channel and the vertical channel are formed at a fight angle relative to one another.

22. The aspirating needle of claim 20, wherein the first lumen and the vertical channel of the second lumen are disposed adjacent one another and extend longitudinally side-by-side for at least a substantial length of the needle.

23. The aspirating needle of claim 18, further including:
  a locking mechanism for selectively locking and restricting axial movement of the stylet in the first lumen.

24. The aspirating needle of claim 23, wherein the locking mechanism includes a first locking feature formed as part of the stylet and a complementary second locking feature formed as part of the elongated body.

25. The aspirating needle of claim 24, wherein the first locking feature comprises a projection formed on an outer surface of the stylet and the second locking feature comprises a channel formed in an inner surface of the elongated body, the channel receiving the projection and being formed to restrict axial movement of the stylet in the first lumen when the stylet is placed in a locked position in the channel.

26. An aspirating needle for collecting a specimen comprising:
  an elongated hollow body that includes a first lumen and a second lumen, the first lumen being open at both ends for placement at a specimen site to collect and permit aspiration of the specimen from the specimen site, the second lumen having first and second vent ports, the second lumen being a vent channel that terminates in a closed distal end that is removed and spaced from a distal tip of the elongated body, the distal tip containing a distal opening of the first lumen, the second vent port being formed in a side wall of the elongated body proximate the closed distal end such that when the needle is placed at the specimen site, the second vent port is positioned at the specimen site, the first vent port being in fluid communication with atmospheric air when the needle is positioned at the specimen site so as to permit pressure within the specimen site to equilibrate with atmospheric pressure by means of the venting action of the second lumen;
  a handle that is part of the elongated body to permit a force to be applied to the needle for directing the needle to the specimen site;
  a filter that is disposed in the second lumen at a proximal end so as to close off a proximal opening the of the second lumen;
  an elongated stylet for insertion into the first lumen; and
  a locking mechanism for selectively locking and restricting axial movement of the stylet relative to the first lumen.

* * * * *